(12) United States Patent
Bonnet et al.

(10) Patent No.: US 9,770,594 B2
(45) Date of Patent: Sep. 26, 2017

(54) ACTIVE IMPLANTABLE MEDICAL DEVICE FOR THE TREATMENT OF HEART FAILURE WITH VAGUS NERVE STIMULATION IN SYNCHRONY WITH CARDIAC ACTIVITY

(71) Applicant: SORIN CRM SAS, Clamart (FR)

(72) Inventors: Jean-Luc Bonnet, Massy (FR); Christine Henry, Paris (FR)

(73) Assignee: SORIN CRM SAS, Clamart (FR)

( * ) Notice: Subject to any disclaimer, the term of this patent is extended or adjusted under 35 U.S.C. 154(b) by 375 days.

(21) Appl. No.: 14/261,185

(22) Filed: Apr. 24, 2014

(65) Prior Publication Data
US 2014/0324116 A1 Oct. 30, 2014

(30) Foreign Application Priority Data
Apr. 25, 2013 (FR) .................................... 13 53777

(51) Int. Cl.
*A61N 1/36* (2006.01)
*A61N 1/365* (2006.01)

(52) U.S. Cl.
CPC ......... *A61N 1/36139* (2013.01); *A61N 1/365* (2013.01); *A61N 1/36114* (2013.01); *A61N 1/36592* (2013.01)

(58) Field of Classification Search
CPC ............ A61N 1/36139; A61N 1/36114; A61N 1/36592; A61N 1/365
See application file for complete search history.

(56) References Cited

U.S. PATENT DOCUMENTS

| | | | |
|---|---|---|---|
| 5,215,098 A * | 6/1993 | Steinhaus | A61B 5/0428 600/509 |
| 6,473,644 B1 | 10/2002 | Terry et al. | |
| 7,738,956 B1 | 6/2010 | Farazi et al. | |
| 2007/0233194 A1 | 10/2007 | Craig | |
| 2010/0114216 A1 | 5/2010 | Krause et al. | |
| 2012/0209343 A1 | 8/2012 | Efimov et al. | |
| 2012/0303080 A1 | 11/2012 | Ben-David et al. | |

OTHER PUBLICATIONS

Search Report for French Patent Application No. FR1353777, dated Jul. 23, 2013, 2 pages.

* cited by examiner

*Primary Examiner* — Mark W Bockelman
(74) *Attorney, Agent, or Firm* — Foley & Lardner LLP

(57) ABSTRACT

A medical device includes a VNS pulse burst generator for stimulation of the vagus nerve, and a controller for analyzing the cardiac rhythm. It further includes a sequencer that uses an estimator to calculate during a given cycle an estimate of the temporal position of the R wave of the next cycle. The controller is configured to define the moment of application of the VNS pulse burst as an instant corresponding to the estimate minus a predetermined advance delay. VNS therapy is thus delivered in a non-vulnerable period, near the end of the period of natural ventricular escape.

17 Claims, 3 Drawing Sheets

ACTIVE IMPLANTABLE MEDICAL DEVICE FOR THE TREATMENT OF HEART FAILURE WITH VAGUS NERVE STIMULATION IN SYNCHRONY WITH CARDIAC ACTIVITY

CROSS-REFERENCE TO RELATED APPLICATION

This application claims the benefit of and priority to French Patent Application No. 1353777, filed Apr. 25, 2013. French Patent Application No. 1353777 is hereby incorporated by reference in its entirety.

BACKGROUND

The invention relates to "active implantable medical devices" as defined by Directive 90/385/EEC of 20 Jun. 1990 the Council of the European Communities. The invention relates to implants for delivering vagus nerve stimulation therapies, which have been called "VNS" therapies (Vagus Nerve Stimulation).

Stimulation of the vagus nerve affects cardiovascular function by reducing the heart rate and myocardial contractility with decreased duration of diastole. These effects can help reduce the progression of cardiac remodeling that may lead heart failure.

In general, the vagus nerve can be stimulated asynchronously or synchronously (e.g., with the heartbeat). In the first case, the device may simply include a lead provided with an electrode implanted on the vagus nerve and of a generator delivering VNS pulses on this electrode. In this configuration there is no possible interference between the VNS electronics and a cardiac lead.

In contrast, in the case of a synchronous stimulation, for example, the device further includes one or more cardiac leads. For example, such a device may include one or more endocardial lead or one or more lead implanted in the coronary network for the collection of the cardiac depolarization waves. Such a device may optionally deliver myocardial stimulation pulses (stimulation of ventricular and/or atrial cavities) using electrodes in the heart, in addition to the VNS stimulation applied separately on the vagus nerve.

U.S. 2012/0303080 A1 and U.S. 2007/0233194 A1 disclose devices for synchronous stimulation of the vagus nerve. In this configuration of synchronous VNS stimulation, pacing should be delivered in a non-vulnerable period of the ventricle.

Particularly, if we consider an electrocardiogram ECG surface or endocardial electrogram EGM, among the different waves representative of the PQRST complex of the cardiac activity, it is known that during the QRS (ventricular depolarization) and the subsequent T wave (ventricular repolarization) the heart is in a refractory period. This ventricular refractory period includes a period called "absolute refractory period" during which no electrical stimulation will have an effect on cardiac cells, followed by a period called "relative refractory period" during which stimulation may excite some heart fibers and induce ventricular arrhythmia.

In the case of stimulation of the vagus nerve and in the case of a system with a ventricular lead, it is commonly accepted that VNS stimulation delivered during the relative refractory period of the ventricle is potentially harmful because charges that could be accumulated on the electrode may trigger ventricular arrhythmias. Stimulation should therefore be avoided during this period. Thus, US 2012/0303080 A1 and US 2007/0233194 A1, cited above disclose synchronizing the application of the VNS pulse burst on the detection of the R wave, in order to apply these pulses during the absolute ventricular refractory period which immediately follows this wave. Despite these prior art devices, it remains challenging and difficult to safely synchronize VNS and heart stimulation treatments.

SUMMARY

An embodiment of the invention is a device configured to deliver VNS stimulation in a period other than the absolute ventricular refractory period and yet without risks of arrhythmia.

The device uses a period corresponding to the end of natural the escape interval of the ventricle, located after the T wave (i.e. way beyond ventricular refractory periods) at a time corresponding to appearance of the atrial depolarization wave (P wave) of the next cardiac cycle. This device may operates with success given that i) the spontaneous activity of the vagus nerve is mainly concentrated in the PQ cardiac interval and ii) the area before the natural ventricular depolarization, typically in a window of a few tens of milliseconds before spontaneous activity thereof, may be regarded as a non-vulnerable period, that is to say not capable of generating arrhythmias.

To determine the time of application of the VNS therapy in this temporal window, one solution would be to have a lead for detecting atrial depolarization, to detect the onset of the P wave, and to synchronize the beginning of the delivery of the VNS pulse burst on this detection. Such a solution would, however, be complicated to implement, requiring the implantation of a lead with atrial sensing electrodes, and an adaptation of the generator, with an additional connector, dedicated internal circuits, etc. In other words, this would be a device that is a "dual chamber" stimulator.

One aim of the invention is to provide a solution to this problem, with a VNS pacemaker synchronized to the atrial signal but that does not require physical means for detecting atrial depolarizations, including an additional lead for detecting the P wave on which the VNS stimulation could be synchronized. The invention can thus advantageously be implemented using circuits of a "single chamber" stimulator, supplemented by VNS pulse bursts triggered by appropriate sequencer operating using inputs from a single ventricular sensing lead.

To this end, the invention provides a device including a generator generating VNS pulse bursts. The device further includes a circuit for analyzing the cardiac rhythm collecting a signal representative of the cardiac electrical activity, including analyzing an endocardial electrogram EGM signal and determining the duration of successive cardiac cycles. The device further includes a VNS sequencer configured to determine a moment of application of a VNS pulse burst by the generator. The VNS sequencer may include an estimation module calculating, during a given cycle, an estimate of the temporal position of the R-wave cycle of the following cycle. The sequencer can be configured to set the application time of the VNS pulse burst as being a time corresponding to the calculated estimate of the temporal position of the R-wave, anticipated by an estimated advance delay.

In a particular embodiment, the analysis of the cardiac rhythm further calculates an average duration and optionally a standard deviation, of the cardiac cycles over a predetermined period or over a predetermined number of cycles. The device can use such analysis of the cardiac rhythm to calculate the advance delay from the duration of the previous cardiac cycles. This may help accurately reflect the variability and evolution in the cardiac rhythm.

A module for analyzing the cardiac rhythm may calculate an average duration of the cardiac cycles over a predetermined period or a predetermined number of cycles, and the VNS sequencer may calculate the estimate of the temporal position of the R wave according to both said average duration and advance delay.

The device may further include a module for detecting spontaneous ventricular events, and can interrupt the delivery of pulses produced by the generator in the event of occurrence of a spontaneous ventricular event subsequent to the instant of application of the VNS pulse burst. It is also possible to provide means for delivering a ventricular pacing pulse in the absence of occurrence of a spontaneous ventricular event at the expiration of a predetermined escape interval.

One embodiment relates to a device having a VNS pulse burst generator for stimulation of the vagus nerve, and electronics analyzing cardiac rhythm. It further includes sequencer having an estimation module for calculating, during a given cycle, an estimate ($R_{prev}$) of the temporal position of the R wave of the next cycle. The sequencer can then define the moment (TVNS) of application of the VNS pulse burst as an instant corresponding to this estimate ($R_{prev}$) adjusted by a predetermined advance delay ($\Delta_{VNS}$). VNS therapy is thus delivered in a non-vulnerable period, near the end of the period of natural ventricular escape.

DETAILED DESCRIPTION

According to various exemplary embodiments, a pacemaker includes a programmable microprocessor provided with circuits for shaping and delivering stimulation pulses to implantable electrodes. The pacemaker may include appropriate programming code (e.g., executable code) for adjusting the VNS stimulator according to the activities described herein. In other words, the algorithms described herein may be contained in computer readable media (e.g., non-transient computer readable media) of the pacemaker device and executed by a microcontroller or a digital signal processor of the pacemaker. For the sake of clarity, the various processing applied will be broken down and diagrammed by a number of different functional blocks in the form of interconnected circuits, however this representation is only illustrative, these circuits having common elements and in practice corresponding to a plurality of functions overall performed by a single software.

Figure 1:
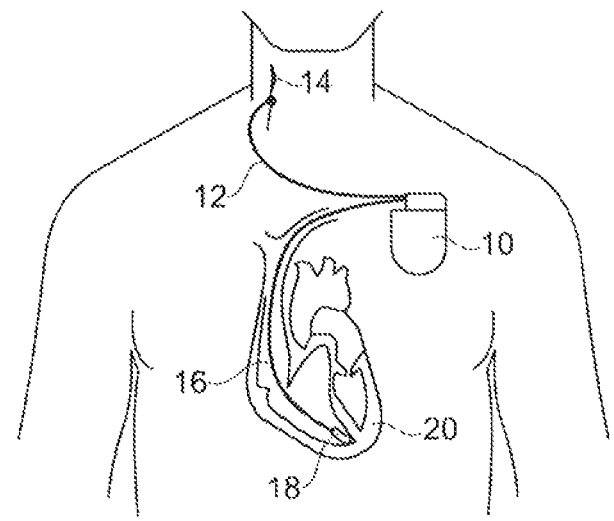
FIG. 1 is an overview presentation of the device, showing the generator, the myocardium, the vagal nerve and the leads used, according to an exemplary embodiment.

In FIG. 1, a device includes a housing of an implantable generator 10 for vagus nerve stimulation. This stimulation is delivered by a lead 12 bearing at its distal portion an electrode implanted on the vagus nerve 14 for stimulation of the latter by application of train pulses produced by the generator 10. To allow delivery of VNS pulses in synchronism with the cardiac rhythm, the generator 10 also has a cardiac lead 16 provided at its distal end of an electrode 18 for collecting the electrical activity of the myocardium 20. This lead collects EGM endocardial electrogram signals that will drive the generator 10 so that it delivers to the vagus nerve 14 VNS stimulation pulses at the same rate as the heart beats and at the most appropriate moment of the cardiac depolarization wave. It should be noted that the use of an endocardial EGM may be substituted for other monitoring techniques suitable for obtaining a signal representative of the cardiac electrical activity.

Figure 2:
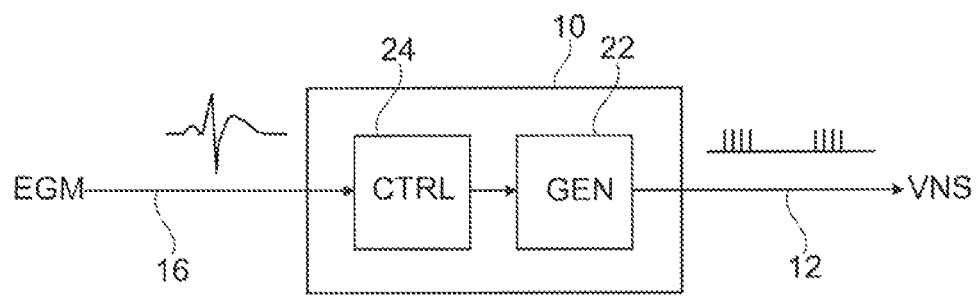
FIG. 2 is a schematic block view corresponding to the main features of the generator of the device, according to an exemplary embodiment.

FIG. 2 schematically illustrates the features of the generator 10 of the device of the invention. The generator 10 includes a generator circuit 22 configured to produce bursts of VNS pulses delivered to the vagus nerve via the lead 12. The generator circuit 22 is controlled by a control circuit 24. An input to the control circuit is the EGM signal gathered by the lead 16.

Figure 3:
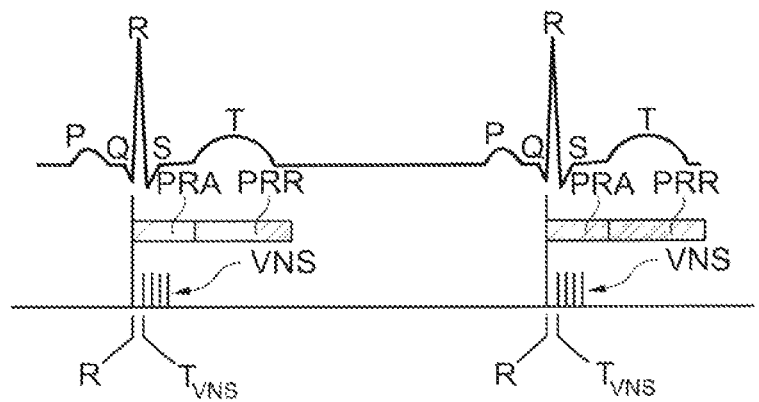
FIG. 3 is a prior art timing diagram showing, in two successive cardiac cycles, the cardiac depolarization wave with its different characteristic periods and the instants of application of the VNS pulse bursts.

FIG. 3 illustrates a prior art example, on two consecutive cardiac cycles, of the cardiac depolarization wave an EGM collected with successively the different representative waves of the cardiac activity: P-wave (depolarization of the atria), QRS (depolarization of the ventricles) and T wave (repolarization of the ventricles).

During the phase of ventricular activity QRST, the heart is in refractory period with an absolute refractory period PRA during which no excitement, including any electrical stimulation, will act on cardiac cells, followed by a relative refractory period PRR during which an excitation may cause depolarization of certain cardiac fibers. If a VNS therapy has to be delivered in the form of a burst of electrical pulses, the instant $T_{VNS}$ of delivery of this burst, and the number and duration of pulses of the burst are often all delivered during the absolute refractory period PRA. This is to avoid triggering ventricular arrhythmia due to a potential ventricular capture by local current fields that may cause deleterious effects, which could occur if the VNS pulses were delivered during the relative refractory period PRR. To meet this requirement, certain prior art stimulation techniques operate in the manner illustrated in FIG. 3, in synchronizing the instant $T_{VNS}$ of the beginning of the burst of VNS pulses relative to the detection of the R wave, i.e. the moment when the detection lead collects spontaneous activity having its origin in the ventricle. Specifically, in U.S. 2012/0303080 A1 cited above, the therapy delivery is calculated based on the PP interval, while in U.S. 2007/0233194 A1 also cited above, VNS stimulation is delivered with a predetermined delay calculated based on the R-wave.

The invention proposes to operate differently, delivering VNS therapy during another period of the cardiac cycle, located outside the natural ventricular refractory periods, particularly outside the relative refractory period PRR, and without risk of arrhythmia.

Figure 4:
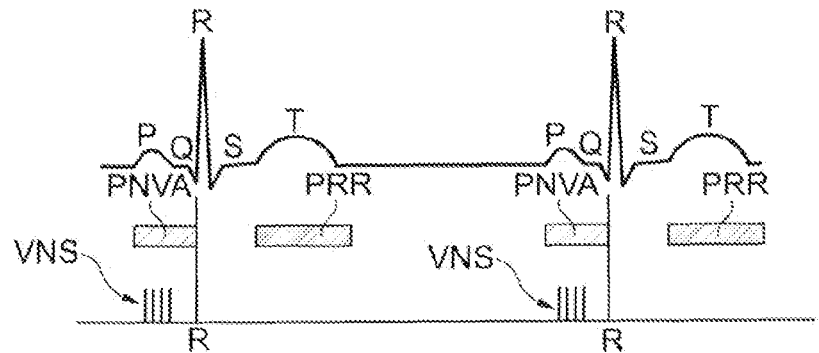
FIG. 4 is a counterpart of FIG. 3, presenting the advantageous technique of the present invention, according to an exemplary embodiment.

As shown in FIG. 4, a VNS therapy is caused at the end of the natural escape interval of the ventricle, corresponding to an atrial non vulnerable PNVA period during which the P wave of atrial depolarization happens, well before the activity phase of the ventricle (QRST complex).

Figure 5:
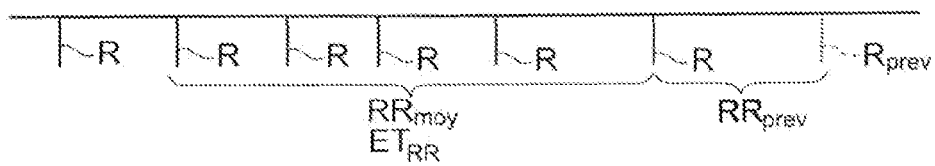
FIG. 5 is a timing diagram illustrating the variability in the RR interval in a series of consecutive cardiac cycles.

Even if the implant does not have the capability to accurately detect the atrial activity, the device may estimate the temporal position of the next ventricular wave and time the delivery of VNS stimulation relative to this estimated position. To do this, as shown in FIG. 5, the device follows the ventricular activity and determines the moments R of collection of spontaneous ventricular activity. Based on these detections, the device calculates the average ventricular period $RR_{moy}$ and its variability, corresponding to the standard deviation $ET_{RR}$ of the parameter RR.

Depending on $RR_{moy}$, and optionally also on $ET_{RR}$, the device calculates an estimate interval $RR_{prev}$, for example by a function of the type:

$$RR_{prev} = RR_{moy} - \alpha \cdot ET_{RR}.$$

If $\alpha=1$, it is estimated that 85% of the RR cycles are longer than $RR_{prev}$, in the case of a Gaussian distribution of the RR intervals. This allows obtaining an estimated temporal position $R_{prev}$ of the R wave of the next cycle.

Figure 6:
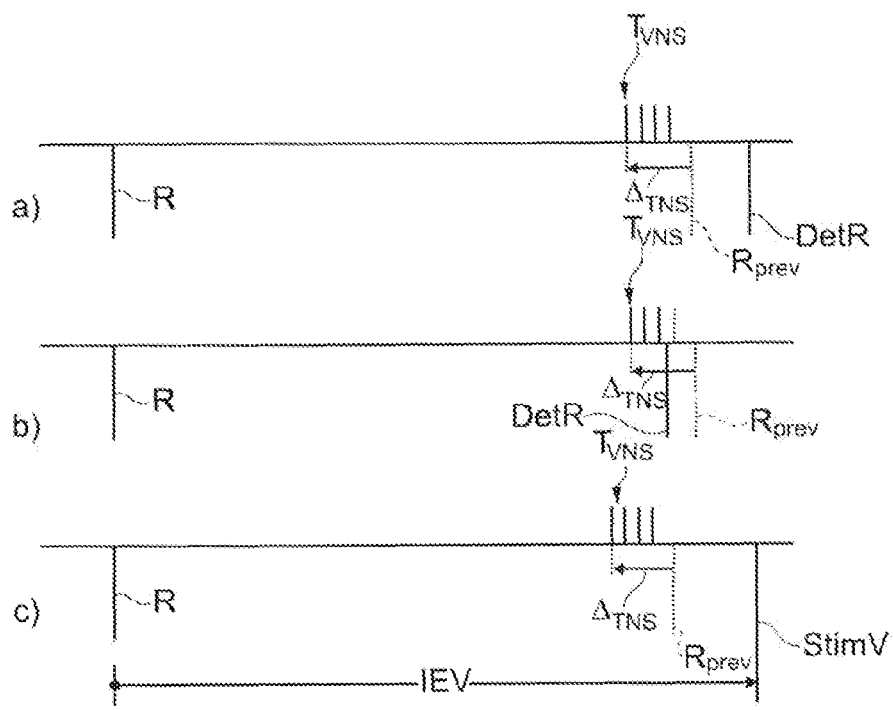
FIGS. 6a to 6c are timing diagrams illustrating the method to determine the instant of application of the VNS stimulation pulses according to the technique of the invention in different situations, respectively: with (a) a normal detection of consecutive R wave, (b) with detection of a premature R wave, and (c) without detection of a consecutive R wave.

As shown in FIG. 6a, the instant $T_{VNS}$ of application of the VNS pulse burst will be determined from this estimated $R_{prev}$, anticipated of an advanced period $\Delta_{VNS}$, typically of the order of $ET_{RR}$ (if $\alpha=1$).

In the normal case (shown in FIG. 6a), the delivery of VNS therapy is followed by the detection of spontaneous activity DetR, in principle close to the estimated position $R_{prev}$.

In the case (shown in FIG. 6b) of a premature spontaneous activity DetR such that it occurs at a time when the VNS pulse burst has not finished being delivered, the device immediately stops this delivery to avoid stimulation during a ventricular refractory period.

In another case (shown in FIG. 6c) wherein no spontaneous ventricular event has been detected at the end of the ventricular escape interval IEV (interval counted from the previous R detection), then a ventricular stimulation StimV is delivered by the device.

Figure 7:
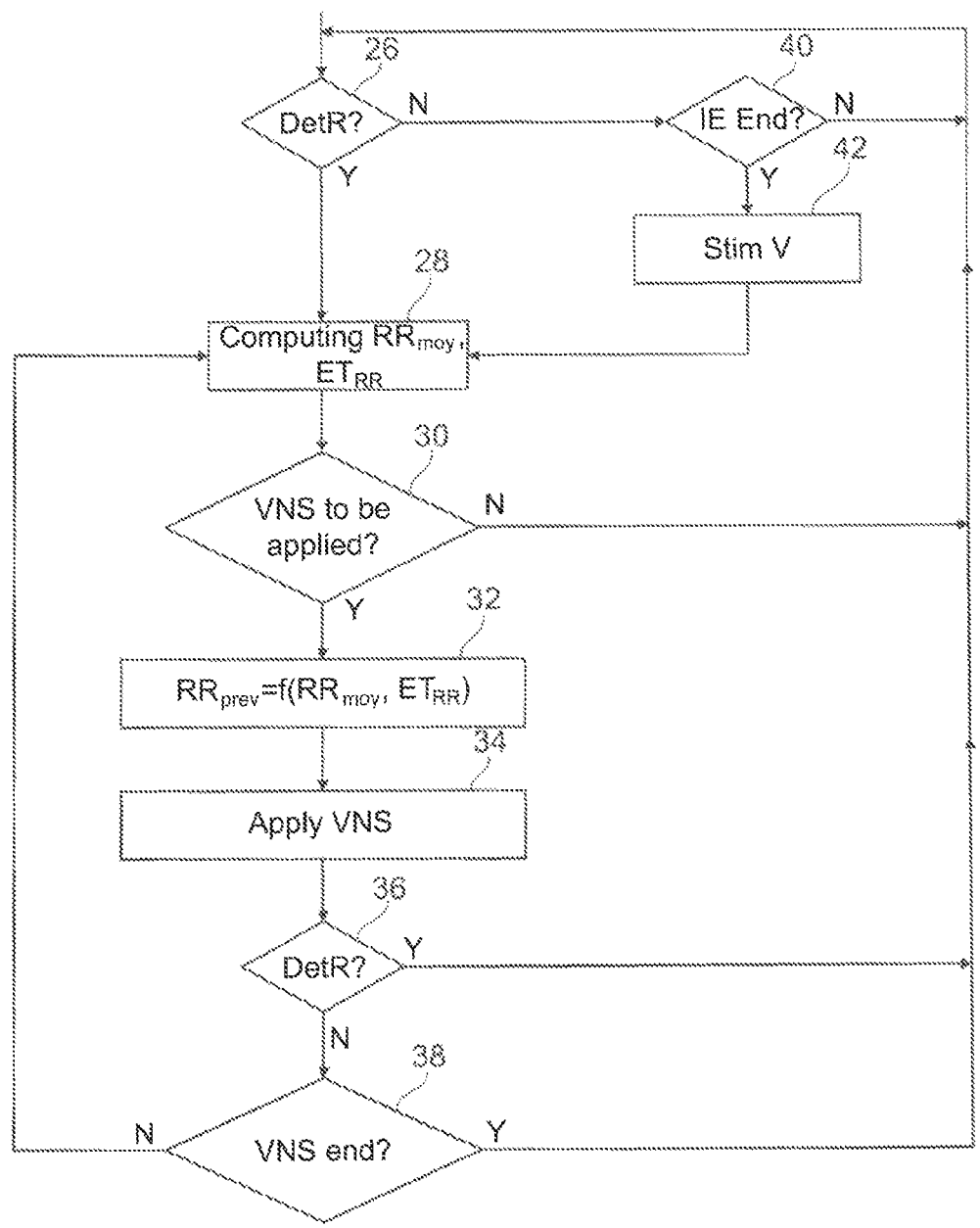
FIG. 7 is a flow diagram a method for providing VNS therapy according to an exemplary embodiment.

FIG. 7 is a flowchart describing the sequence of different actions that has just been described. Upon detection of a ventricular activity DetR (test 26), the device calculates or recalculates the values of the interval $RR_{moy}$ and of the standard deviation $ET_{RR}$ (block 28).

If VNS stimulation should be applied (test 30), then the device estimates the expected duration of the next RR interval from the mean and standard deviation of the preceding RR intervals (block 32). VNS therapy is then applied, by triggering the delivery of VNS pulse bursts according to the estimated instant, determined in the previous step, of the temporal position of the next R wave (block 34).

If during the delivery of the pulse burst ventricular depolarization DetR is detected (test 36), then this delivery is interrupted and the method is reset (back to test 26). Otherwise, the delivery of the VNS therapy is continued until the last pulse of the burst, and the method is repeated (back to block 28). Upon arriving at the end of the VNS therapy (test 38), the method may be fully reset (back to test 26). In any case, in the absence of detection DetR (test 26) at the end of the ventricular escape interval IE (test 40), a ventricle stimulation StimV (see FIG. 6(c)) is delivered to the device (block 42).

The invention claimed is:

1. An active implantable medical device for the treatment of heart failure with vagus nerve stimulation (VNS), comprising:
   a generator configured to generate VNS pulse bursts;
   a controller for analyzing a cardiac rhythm of a heart, the controller configured to collect a signal representative of the heart's electrical activity and to determine lengths of successive cardiac cycles; and
   wherein the controller is configured to determine an instant of application of a VNS pulse burst by the generator;
   wherein the controller comprises an estimator configured to calculate, during a given cycle, an estimate of a temporal position of an R wave of the next cycle using the determined lengths of successive cardiac cycles; and
   wherein the controller is further configured to define the application of the VNS pulse burst as corresponding to the calculated estimate of the temporal position of the R wave reduced by an estimated in-advance delay for the VNS pulse burst.

2. The device of claim 1, wherein the controller is further configured to analyze the cardiac rhythm to calculate an average duration of the cardiac cycles over a predetermined period or a predetermined number of cycles; and wherein the controller is further adapted to calculate said in-advance delay to reflect an observed change in heart rate.

3. The device of claim 2, wherein a VNS sequencer is configured to calculate the estimate of the temporal position of the R wave according to both the average duration and said in-advance delay.

4. The device of claim 2, wherein a VNS sequencer is configured to calculate the estimate of the temporal position of the R wave according to the in-advance delay.

5. The device of claim 1, wherein a VNS sequencer is configured to detect spontaneous ventricular events; and wherein the VNS sequencer is configured to interrupt delivery of the pulses produced by the generator in case of an occurrence of a spontaneous ventricular event after the instant of application of the VNS pulse burst.

6. The device of claim 5, wherein the VNS sequencer is configured to cause delivery of a ventricular pacing pulse in the absence of an occurrence of a spontaneous ventricular event prior to an expiration of a predetermined escape interval.

7. The device of claim 1, wherein the signal representative of the cardiac electrical activity is an endocardial electrogram signal EGM.

8. The device of claim 1, wherein the controller is further configured to analyze the cardiac rhythm to calculate an average duration and a standard deviation of the cardiac cycles over a predetermined period or a predetermined number of cycles.

9. The device of claim 8, wherein a VNS sequencer is configured to calculate the estimate of the temporal position of the R wave according to both the average duration and the standard deviation.

10. A method for VNS stimulation, including:
   analyzing a cardiac rhythm of a heart by a controller of an implantable medical device configured to collect a signal representative of the heart's electrical activity and to determine lengths of successive cardiac cycles;

calculating during a given cycle, by the controller, an estimate of a temporal position of an R wave of the next cycle using the determined lengths of successive cardiac cycles;

subtracting, by the controller, an estimated in-advance delay from the estimate of the temporal position of the R wave of the next cycle;

determining, by the controller, a time for application of a VNS pulse burst based on the estimate of the temporal position of the R wave of the next cycle reduced by the estimated in-advance delay; and generating, by a generator, the VNS pulse burst at the time for application.

11. The method of claim 10, further comprising:

calculating an average duration of the cardiac cycles over a predetermined period or a predetermined number of cycles; and adjusting the in-advance delay based on the calculated average duration.

12. The method of claim 11, further comprising:

calculating the time for application of the VNS pulse according to both the average duration and said in-advance delay.

13. The method of claim 11, further comprising:

detecting spontaneous ventricular events; and interrupting delivery of the pulses produced by the generator in response to a detected occurrence of a spontaneous ventricular event after the application of the VNS burst pulse.

14. The method of claim 10, further comprising:

detecting spontaneous ventricular events; and delivering, by the generator, a ventricular pacing pulse in the absence of an occurrence of a spontaneous ventricular event prior to an expiration of a predetermined escape interval.

15. The method of claim 10, wherein the signal representative of the cardiac electrical activity is an endocardial electrogram signal EGM.

16. The method of claim 10, further comprising:

calculating a standard deviation of the cardiac cycles over a predetermined period or a predetermined number of cycles; and adjusting the in-advance delay based on the calculated standard deviation.

17. The method of claim 16, further comprising:

calculating the time for application of the VNS pulse according to both the average duration and the standard deviation.

* * * * *